(12) United States Patent
Walter

(10) Patent No.: US 7,736,576 B2
(45) Date of Patent: Jun. 15, 2010

(54) SURFACE MODIFIED EXPANDED POLYTETRAFLUOROETHYLENE DEVICES AND METHODS OF PRODUCING THE SAME

(75) Inventor: James Todd Walter, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 12/478,528

(22) Filed: Jun. 4, 2009

(65) Prior Publication Data

US 2009/0258960 A1   Oct. 15, 2009

Related U.S. Application Data

(60) Continuation of application No. 10/895,737, filed on Jul. 20, 2004, now abandoned, which is a division of application No. 09/369,231, filed on Aug. 5, 1999, now Pat. No. 6,780,497.

(51) Int. Cl.
*B23K 26/36* (2006.01)
*A61F 2/02* (2006.01)
*H01S 3/00* (2006.01)

(52) U.S. Cl. .................. 264/400; 216/94; 623/23.74; 264/446; 264/482

(58) Field of Classification Search ................. 264/400, 264/435, 446, 479, 482; 623/23.74, 926; 216/65, 94
See application file for complete search history.

(56) References Cited

U.S. PATENT DOCUMENTS

| 4,064,030 A | 12/1977 | Nakai et al. |
| 4,187,390 A | 2/1980 | Gore |
| 4,208,745 A | 6/1980 | Okita |
| 4,304,978 A | 12/1981 | Saunders |
| 4,332,035 A | 6/1982 | Mano |
| 4,480,169 A | 10/1984 | Macken |
| 4,550,447 A | 11/1985 | Seiler, Jr. et al. |
| 4,596,577 A | 6/1986 | Sato |
| 4,647,416 A | 3/1987 | Seiler, Jr. et al. |
| 4,713,070 A | 12/1987 | Mano |
| 4,718,907 A | 1/1988 | Karwoski et al. |
| 4,729,766 A | 3/1988 | Bergentz et al. |

(Continued)

FOREIGN PATENT DOCUMENTS

EP   159034   10/1985

(Continued)

OTHER PUBLICATIONS

Blitshteyn M and Wettermann B. Surface treatment of polyolefins. Modern Plastics. Mid-October Encyclopedia Issue 1991:424.

(Continued)

*Primary Examiner*—Matthew J. Daniels
(74) *Attorney, Agent, or Firm*—David J. Johns

(57) ABSTRACT

Improved processes for surface treating expanded polytetrafluoroethylene (PTFE) is disclosed and improved surface-treated devices made from the processes. The processes employ a laser to surface-modify an expanded PTFE structure to create a macro-roughened surface that has the capability to remain microporous throughout. The unique process of the present invention creates a ridge and valley structure on the surfaces of devices that includes unique gnarled nodes along valley floors.

5 Claims, 16 Drawing Sheets

U.S. PATENT DOCUMENTS

| | | | |
|---|---|---|---|
| 4,734,112 | A | 3/1988 | Okita et al. |
| 4,767,418 | A | 8/1988 | Deininger et al. |
| 4,822,361 | A | 4/1989 | Okita et al. |
| 4,869,714 | A | 9/1989 | Deininger et al. |
| 4,919,659 | A | 4/1990 | Horbett et al. |
| 4,933,060 | A | 6/1990 | Prohaska et al. |
| 4,946,903 | A | 8/1990 | Gardella, Jr. et al. |
| 4,955,909 | A | 9/1990 | Ersek et al. |
| 5,002,572 | A | 3/1991 | Picha |
| 5,118,524 | A | 6/1992 | Thompson et al. |
| 5,219,894 | A | 6/1993 | Yamada et al. |
| 5,252,626 | A | 10/1993 | Yamada et al. |
| 5,296,510 | A | 3/1994 | Yamada et al. |
| 5,437,900 | A | 8/1995 | Kuzowski |
| 5,462,781 | A | 10/1995 | Zukowski |
| 5,466,509 | A | 11/1995 | Kowligi et al. |
| 5,730,924 | A | 3/1998 | Katoh et al. |
| 5,747,128 | A | 5/1998 | Campbell et al. |
| 5,833,664 | A | 11/1998 | Seare, Jr. |

FOREIGN PATENT DOCUMENTS

| | | |
|---|---|---|
| EP | 313263 | 3/1993 |
| WO | 9218320 | 10/1992 |

OTHER PUBLICATIONS

Collins G C S et al. An analysis of PTFE surfaces modified by exposure to glow discharges. European Polymer Journal 1973; 9:1173-1185.

Dekker A et al. Adhesion of endothelial cells and adsorption of serum proteins on gas plasma-treated PTFE. Biomaterials 1991; 62:259-263.

Garfinkle A M et al. Improved patency in small diameter dacron vascular grafts after a tetrafluoroethylene glow discharge treatment. Presented at the Second World Congress on Biomaterials, Washington DC, Apr. 27-May 1, 1984.

Hoffman A. Biomedical applications of plasma gas discharge processes: A tutorial presentation. Polymeric Materials 1987; 669-703.

Iriyama Y et al. Plasma surface treatment on nylon fabrics by fluorocarbon compound. Journal of Applied Polymer Science 1990; 39:249-264.

Kuper S and Stuke M. Ablation of polytetrafluoroethylene (Teflon) with femtosecond UV excimer laser pulses. Appl Phys Letter 1989; 54(1):4-6.

Kusabiraki M. Plasma polymerized hexamethyldisiloxane coating on PTFE films in a triode glow discharge system. Polymeric Materials 1990; 62:37-42.

Kusabiraki M. Surface modification of PTFE films by discharges. Japan Journal of Applied Physics, Part 1. 1990; 29(12):2809-2814.

Mateo N B. Using gas plasma to reengineer surfaces. Medical Product Manufacturing News Sep./Oct. 1990.

Morra M et al. Contact angle hysteresis in oxygen plasma treated polytetrafluoroethylene. Langmuir 1989; 5:872-876.

Morra M et al. Surface characterization of plasma-treated PTFE. Surface and Interface Analysis 1990; 16:412-417.

Niino H, Yabe A. Chemical surface modification of fluorocarbon polymers by excimer laser processing. Applied Surface Science 1996; pp. 550-557.

Niino H et al. Surface modification of polytetrafluoroethylene by excimer laser processing: enhancement of adhesion. Applied Surface Science 1997; 109/110:259-263.

Nishii M. Surface modification of polytetrafluoroethylene by KrF-Laser Irradiation. Chemistry Letters 1992; pp. 2089-2090.

Picha G J. Ion-Beam Microtexturing of biomaterials. Medical Device and Diagnostic Industry 1984; 6(4)39-42.

Pireaux JJ et al. Excimer laser ($\lambda$=193 nm) versus Al K$\alpha$ X-ray damages on polymer surfaces: an XPS (core and valence levels) analysis of polytetrafluoroethylene, polypropylene and polyethylene. Nuclear Instruments and Methods in Physics Research B 1995; 105:186-191.

Schakenraad J M et al. Patency of small caliber, superhydrophobic ePTFE vascular grafts: A pilot study in the rabbit carotid artery. Cells and Materials 1992; 2(3):193-199.

Taylor S R et al. Effect of surface texture on the soft tissue response to polymer implants. Journal of Biomedical Materials Research 1983; 17:205-227.

Torem S et al. Factors influencing acute thrombus formation on carotid artery vascular grafts. Trans Am Soc Artif Internal Organs 1988; 34:916-920.

Torrisi L and Foti G. Ion beam etching of polytetrafluoroethylene. Journal of Mater. 1990; 5(11):2723-2728.

Tran C, Walt D. Plasma modification and collagen binding to PTFE grafts. Journal of Colloid and Interface Science 1989; 132(2):373-381.

Tung B. Surface modification of fluoropolymers with plasma generated via microwave discharge. SAMPE Quarterly 1988; 19(3):36-39.

Vargo T G et al. Hydrogen/liquid vapor radio frequency glow discharge plasma oxidation (PVDF) surfaces. Journal of Polymer Science; Part A:Polymer Chemistry 1991; 29:555-570.

Vargo T G et al. Silane refunctionalization of radio frequency glow discharge hydrolysed ePTFE membrane surfaces. Polymeric Materials 1990; 62:259-263.

Yeh Y S. Blood compatibility of surfaces modified by plasma polymerization. Journal of Biomedical Materials Research 1988; 22:795-818.

Youxian D. Surface modification of poly(tetrafluoroethylene) by gas plasma treatment. Polymer 1991; 32(6):1126-1130.

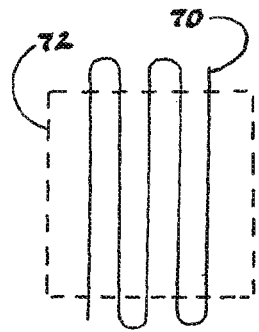 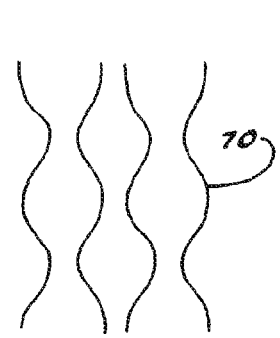 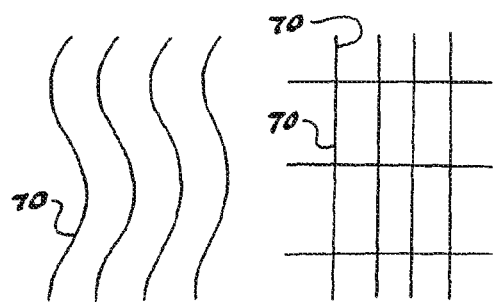
Fig. 8A  Fig. 8B  Fig. 8C  Fig. 8D
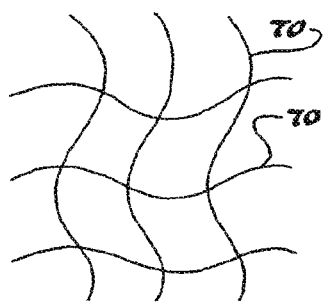 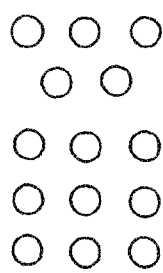 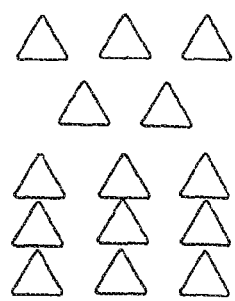
Fig. 8E  Fig 8F  Fig. 8G
ABC24  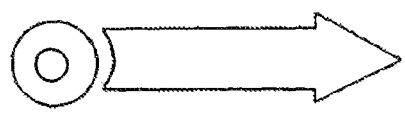
Fig. 8H  Fig. 8I

SURFACE MODIFIED EXPANDED POLYTETRAFLUOROETHYLENE DEVICES AND METHODS OF PRODUCING THE SAME

CROSS REFERENCE TO RELATED APPLICATIONS

This application is a continuation of application Ser. No. 10/895,737 filed Jul. 20, 2004 now abandoned, which is a division of application Ser. No. 09/369,231 filed Aug. 5, 1999, now U.S. Pat. No. 6,780,497 issued Aug. 24, 2004.

BACKGROUND OF THE INVENTION

1. Field of the Invention

The present invention relates to a surface modified expanded polytetrafluoroethylene material, and methods used to produce it.

2. Description of Related Art

Expanded polytetrafluoroethylene (PTFE) products are widely employed today in a variety of devices, including filters, fabrics, implantable sheets, and vascular grafts. Expanded PTFE is formed by heating and rapidly expanding a PTFE precursor material to form a microstructure of polymeric nodes interconnected by polymeric fibrils with microscopic void spaces therebetween. Expanded PTFE can be formed in the manner described in U.S. Pat. Nos. 3,953,566, 3,962,153, 4,096,227, and 4,187,390, all incorporated by reference.

The relative dimensions of the node and fibrils can be tailored to affect both the porosity and surface properties of expanded PTFE. For example, a highly porous surface can result from the creation of long, widely spaced, substantially parallel fibrils. A highly porous surface is often beneficial in certain applications. For example, a high degree of porosity may enhance lamination bond strength or improve certain filter performance properties. In specific medical applications, more open structure may be beneficial since the structure can encourage tissue ingrowth and attachment. On a flat sheet, however, there is a limit to the amount of ingrowth structure that can be achieved through only manipulation of nodes and fibrils during expansion. To further enhance tissue ingrowth beyond that of a highly porous surface, a roughened or textured surface is believed to be required. Thus, in medical applications requiring rapid tissue ingrowth, an ideal expanded PTFE surface may have both a high degree of porosity and further surface modification to provide some degree of macroscopic texturing.

In addition to enhancing the rate of tissue attachment, a textured surface may be desirable in other applications, for instance to enhance bond strength, abrasion, heat transfer, optical, or other properties. Increased roughness may also be desirable to increase surface friction, flow turbulence, sound abatement, or exposed surface area.

Various methods of altering the surface properties of expanded PTFE have been suggested in the past. For example, an expanded PTFE surface treatment process is taught in U.S. Pat. Nos. 5,462,781 and 5,437,900 to Zukowski. Disclosed is a plasma treatment process that removes fibrils to a selected depth to leave freestanding nodal ridges. These freestanding nodes are easily bent or deflected due to the lack of supporting fibrils. Such a treated surface affects the hydrophobicity, bondability, and appearance, but may not necessarily elicit an optimum tissue response due to an excessively "soft" exposed surface.

U.S. Pat. Nos. 4,550,447 and 4,647,416 to Seiler, Jr., et al., teach a PTFE surface treatment that creates full density PTFE ribs on the outer surface of an expanded PTFE tube. Although this process may increase macro-roughness by the producing stiff ridges, the ridges are unexpanded and are thus non-porous. Non porous unexpanded ridges are believed to be undesirable since they can achieve only minimal tissue attachment and ingrowth.

U.S. Pat. Nos. 4,332,035 and 4,713,070 to Mano, teach an expanded PTFE process wherein differential heat is applied to opposing surfaces of a tubular wall. The process results in a randomly oriented ridge and valley texture. The ridges comprise node groupings having interconnecting fibrils. The valleys have long fibrils, which interconnect the node groupings. Although this process may increase surface "roughness" due to the relatively stiff ridges, the valleys remain soft due to the long interconnecting fibrils. Thus the valleys produced by the Mano process contribute little to the overall macro-roughness of the device and therefore probably do not enhance the rate of tissue attachment.

For specific applications, it is believed desirable to generate a highly porous expanded PTFE surface having optimum roughness or texturing. A ridge and valley surface texture can enhance the macro-roughness. However, it is believed desirable that ridges are both relatively stiff and at least somewhat porous. Similarly, it is desirable that the valleys remain porous yet provide some addition means to contribute to the macro-roughness of the device. The ridges and valleys would ideally have a pattern that could be controlled and tailored for specific applications.

SUMMARY OF THE INVENTION

The present invention is a process to alter expanded polytetrafluoroethylene (PTFE) surfaces to control surface properties and unique devices with surfaces so modified. The present invention produces articles having a high degree of surface roughness while being capable of maintaining a porous microstructure throughout.

The process of the present invention employs an unfocused laser beam to both alter and remove selected expanded PTFE fibrils and nodes, resulting in a ridge and valley texture. The ridges comprise clustered nodes that are internally supported by shortened interconnecting fibrils. This structure imparts both porosity and stiffness to the ridges. The valleys are formed by the substantial removal of nodes along with their interconnecting fibrils, resulting in a porous valley floor. However, the process also creates a series of distorted or gnarled nodes along the valley floor. These gnarled node structures, remaining in and projecting from the valleys, contribute to the surface "roughness" and texture of the valleys, but do not significantly compromise the porosity. Thus the modified surface has a texture that can be simultaneously macro-rough and micro-porous along both the ridges and valleys.

The process of the present invention can be used to generate repeatable, consistent textures onto an expanded PTFE surface after the base expanded PTFE material has been created. Thus common expanded PTFE materials can be subsequently processed into a variety of textures, each texture being optimized for a specific application. These and other aspects and advantages will become more apparent when considered with the following detailed description, drawings, and appended claims.

DESCRIPTION OF THE DRAWINGS

The present invention may be better understood when considered in light of the attached figures, in which:

FIGS. 8A through 8I are top plan views of alternative patterns that may be employed with the present invention;

DETAILED DESCRIPTION OF THE INVENTION

The present invention comprises a unique method for forming a unique material from an expanded polytetrafluoroethylene (PTFE) material. The present invention may be better understood through a review of previous PTFE surface treatment techniques, as are illustrated in FIGS. 1A through 3B and described below.

Figure 1A:
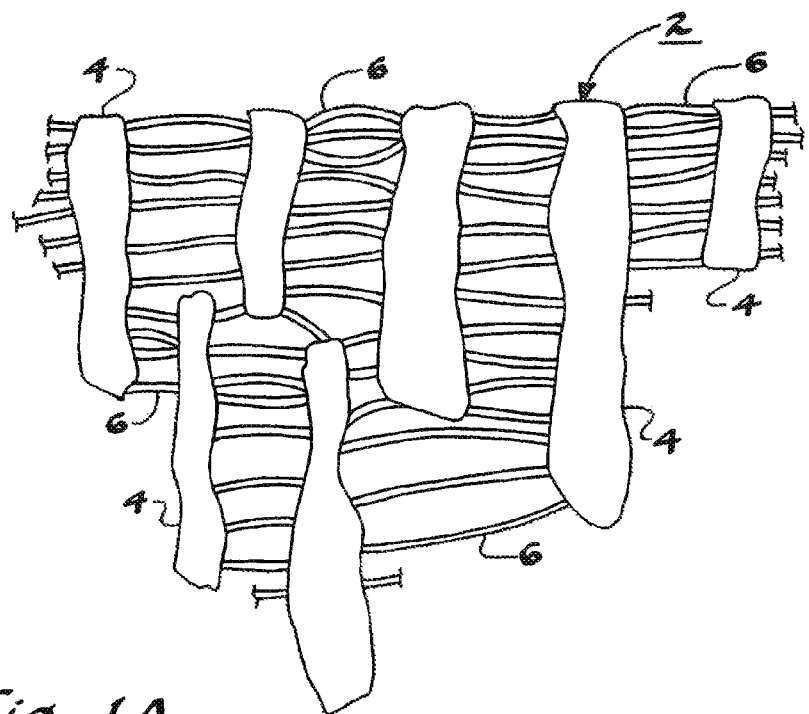
FIGS. 1A and 1B are enlarged partial side cross-section views of an expanded PTFE material, before and after the surface treatment taught by U.S. Pat. Nos. 5,462,781 and 5,437,900 to Zukowski.
Figure 1B:
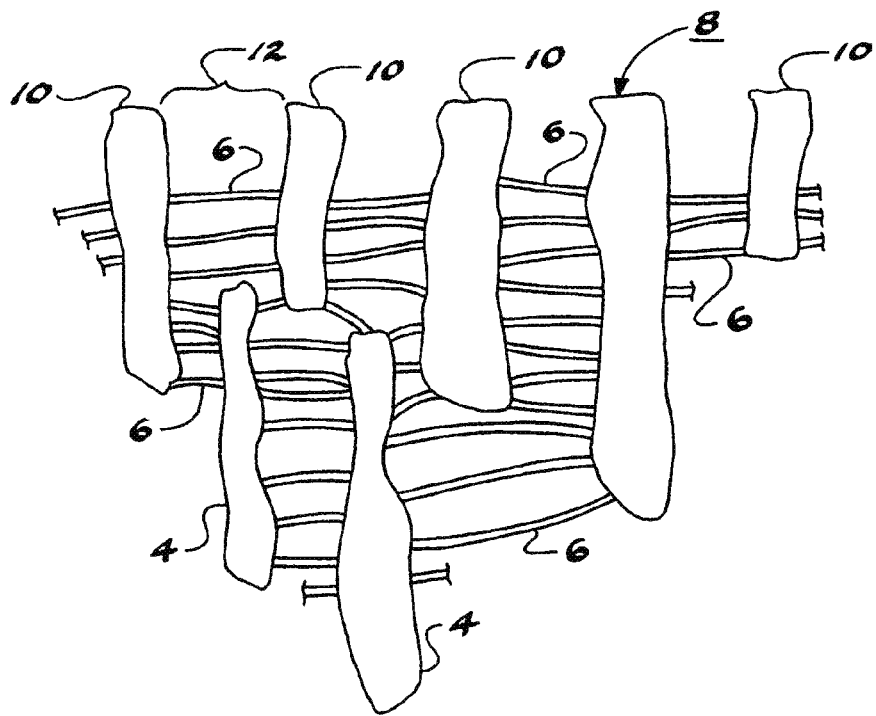

An expanded PTFE surface treatment process is taught in U.S. Pat. Nos. 5,462,781 and 5,437,900 to Zukowski. Zukowski employs a plasma surface treatment process, in which the surface fibrils are removed to a selected depth to leave freestanding nodal ridges. The modification process taught by Zukowski results in freestanding nodes on its surface that maintain their untreated, vertical orientation. FIGS. 1A and B depict cross-section views of an expanded PTFE material before and after, respectively, a Zukowski surface treatment. Shown in FIG. 1A is an expanded PTFE surface 2 prior to the plasma treatment having typical nodes 4 interconnected by fibrils 6. Shown in FIG. 1B is an expanded PTFE surface 8 after the plasma treatment having the same nodes 4 and fibrils 6 in its depth, but having a modified surface with freestanding nodes 10 and open valleys 12 between them. Surface fibrils have been removed by the plasma treatment to a selected depth. Although having the cross-sectional appearance of a "rough" or textured surface, the freestanding nodes 10 are in actuality easily bent or deflected due to the lack of interconnecting fibrils or other support structure. The resulting treated surface has a soft, felt-like texture. Such a treated surface affects the hydrophobicity, bondability, and appearance, but will not necessarily elicit an optimum tissue response due to the lack of true roughness.

Figure 2:
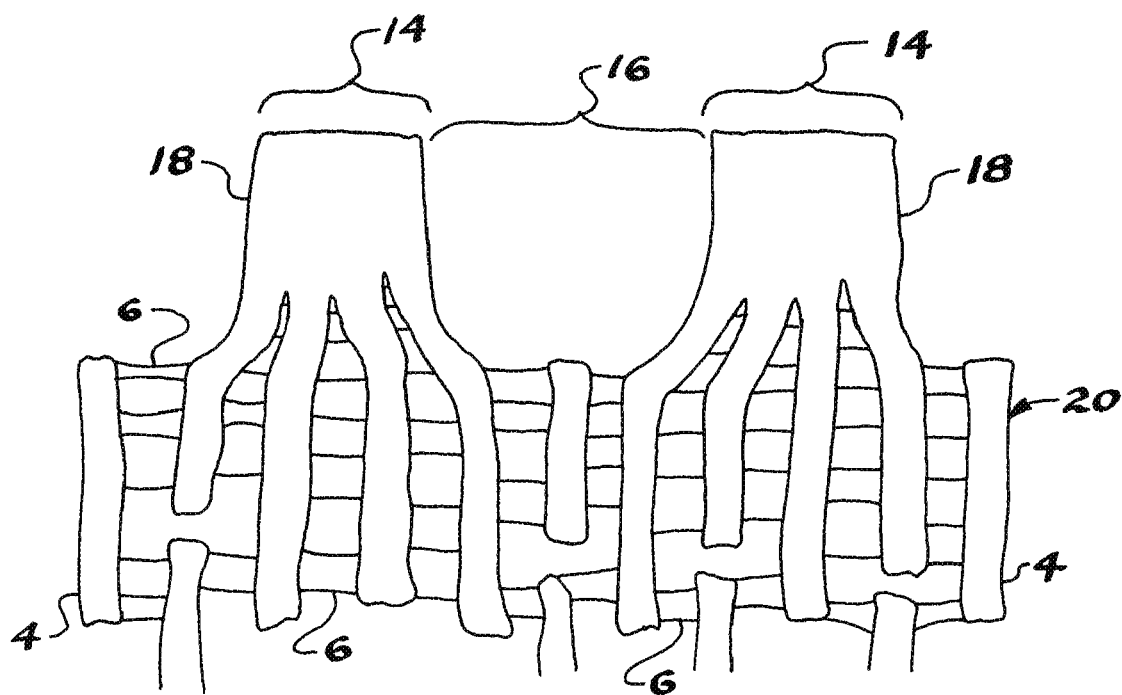
FIG. 2 is an enlarged partial side cross-section view of the wall of an expanded PTFE tube, after processing as taught by U.S. Pat. Nos. 4,550,447 and 4,647,416 to Seiler, Jr., et al.

U.S. Pat. Nos. 4,550,447 and 4,647,416 to Seiler, Jr. et al., teach a PTFE surface treatment process using a laser to partially scribe circumferentially through the wall of an unexpanded PTFE tube. The tube is subsequently expanded, resulting in densified, unexpanded ribs on the outer surface of the tube. The stiff, densified ridges may act as circumferential rings to improve the radial strength and kink resistance of the tube. The resulting wall cross section has a castellated ridge and valley appearance. Shown in FIG. 2 is what is believed to be a typical cross-section view of the wall of an expanded PTFE tube after processing as taught by Seiler, Jr. et al. Shown are outer ridges 14, valleys 16, densified ridge portions 18, and internal expanded PTFE 20, having nodes 4 interconnected by fibrils 6. Although the macro-roughness has been increased by the presence of the stiff ridges 14, the ridges are unexpanded and are thus non-porous. This process results in non-porous unexpanded ridges that may compromise or eliminate any tissue attachment and ingrowth into the ridges.

U.S. Pat. Nos. 4,332,035 and 4,713,070 to Mano teach an expanded PTFE treatment wherein differential heat is applied to opposing surfaces of a tubular wall. The process results in an alteration of the orientation of strength between the two walls. This difference in strength orientation increases the kink resistance and radial strength of the tube. Also altered by the Mano process is the surface texture of the tubular wall. It is believed that the process as taught by Mano was utilized in the production of commercially available vascular grafts. Results from an analysis of such a vascular graft are depicted in FIGS. 3 A and B.

Figure 3A:
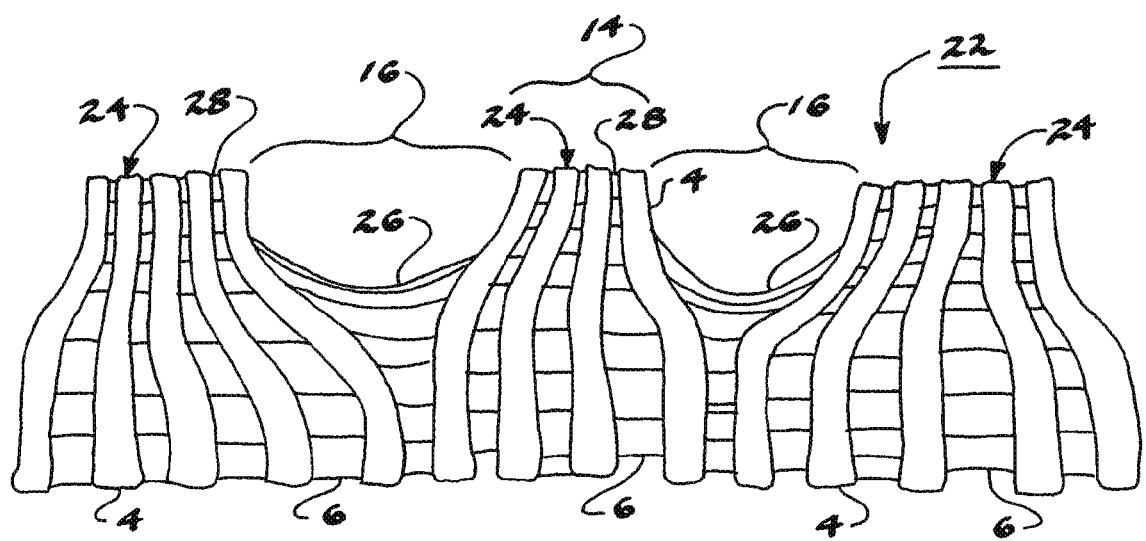
FIG. 3A is an enlarged partial side cross-section view of an outer surface of a vascular graft, as taught by U.S. Pat. Nos. 4,332,035 and 4,713,070 to Mano.
Figure 3B:
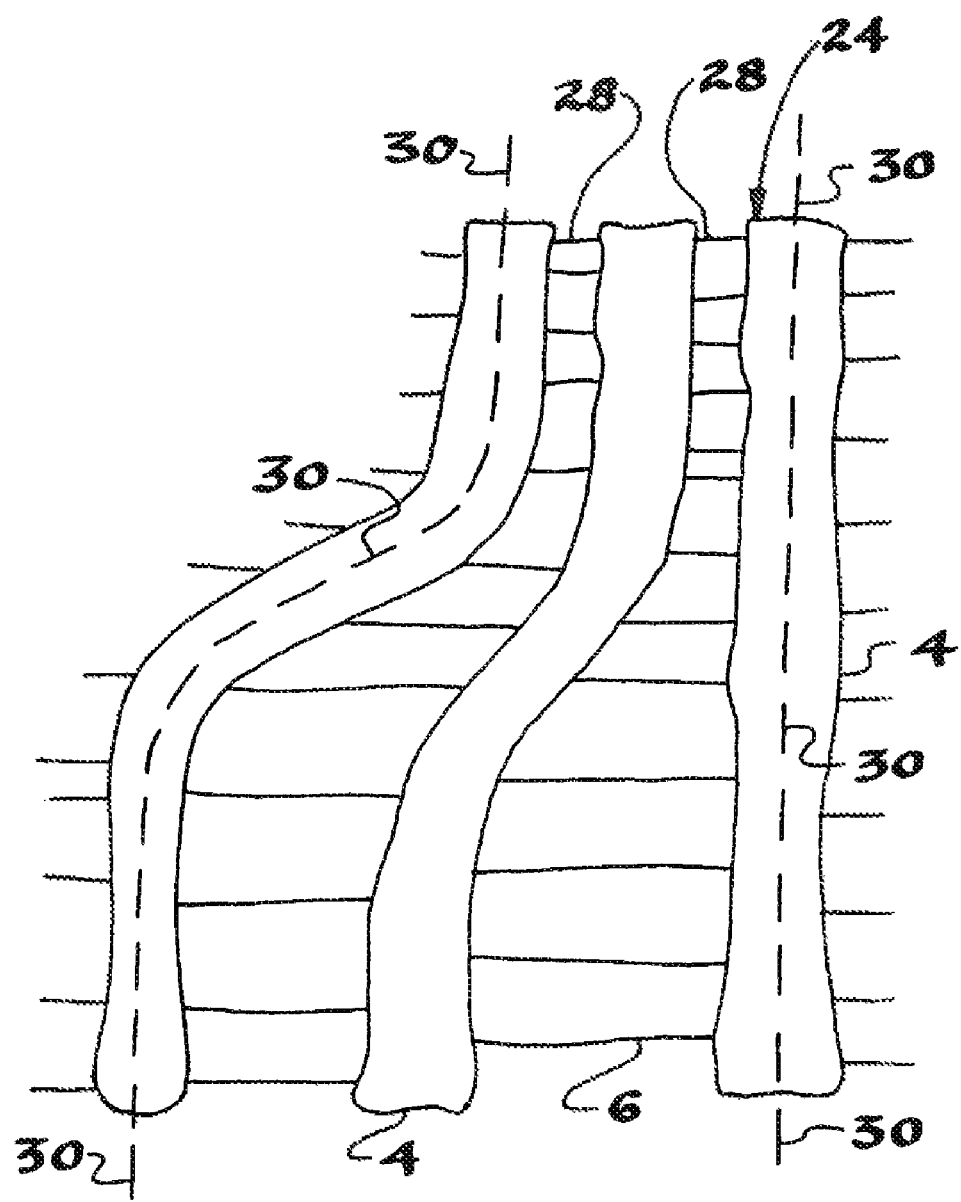
FIG. 3B is an enlarged partial side cross-section view of an angular, coalesced node grouping, and angular node axes as taught by U.S. Pat. Nos. 4,332,035 and 4,713,070 to Mano.

Shown in FIG. 3A is a partial cross-section view of an outer surface of the vascular graft. Shown is the treated vascular graft 22, having a microstructure of nodes 4 interconnected by fibrils 6, ridges 14, and valleys 16. The ridges 14 are comprised of angular, coalesced node groupings or clusters 24. The valleys 16 have long fibrils 26, which interconnect the angular, coalesced node groupings 24. The ridges 14 are relatively stiff due to the interconnecting fibrils 28 present within the coalesced node clusters 24. The interconnecting fibrils 28 within the node clusters preserve a degree of porosity. Thus the node clusters typically have some porosity although less porosity than the valleys or untreated lower sections within the graft wall. Although the surface "roughness" has been increased due to the relatively stiff coalesced node clusters, the valleys remain soft due to the long interconnecting fibrils 26. Thus the valleys resulting from the Mano process are believed contribute little to the overall macro-roughness of the final device. The process as taught by Mano also results in a random, undefined pattern of ridges and valleys. Shown in FIG. 3 B, is a partial cross-section view of an angular, coalesced node grouping 24 and angular node axes 30. As can be seen by following angular node axis 30, the axis 30 of the coalesced node articulate or bend between approximately 0 and 90° along the axis length.

None of the above-described processes provides all the features that may be desired in an optimal surface-treated product. Although incorporating various desirable aspects, the known processes do not generate an optimized and ordered surface texture having a high degree of macro-roughness along with a high degree of porosity along both the ridges and the valleys. The process of the present invention provides such an enhanced surface.

FIGS. 4A through 4E show enlarged partial cross-section views of an expanded PTFE surface at sequential stages that are believed to occur during the process of the present invention. Precursor expanded PTFE material may take any of various forms, including material made in accordance with any of U.S. Pat. Nos. 3,953,566, 3,962,153, 4,096,227, 4,187,390, and 4,902,423, all incorporated by reference. Additionally, suitable precursor material is also commercially available from a number of sources in a wide variety of forms, including, for example, from W. L. Gore & Associates, Inc., Elkton, Md., under the trademarks GORE-TEX® and GORE-TEX® GR gasketing materials, and from W. L. Gore & Associates, Inc., Flagstaff, Ariz., under the trademarks GORE-TEX®, DUALMESH®, and MYCROMESH® implantable patch materials. It is believed preferred that the nodes of the precursor material be oriented substantially perpendicular to the surface to be treated.

Figure 4A:
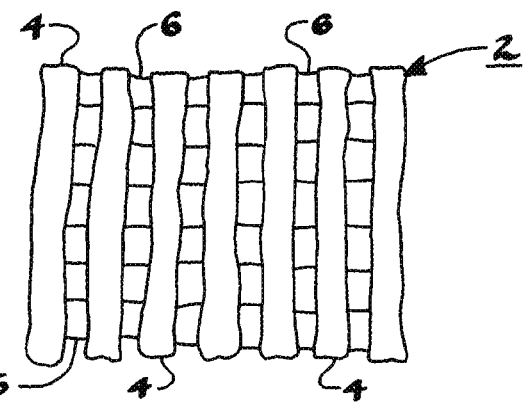
FIGS. 4A through 4F are enlarged partial side cross-section views of an expanded PTFE surface at various stages of alteration that are believed to be occurring during the process of the present invention.

FIG. 4A is a partial cross-section view of an initial, untreated expanded PTFE material 2 having a microstructure of nodes 4 interconnected by fibrils 6.

Figure 4B:
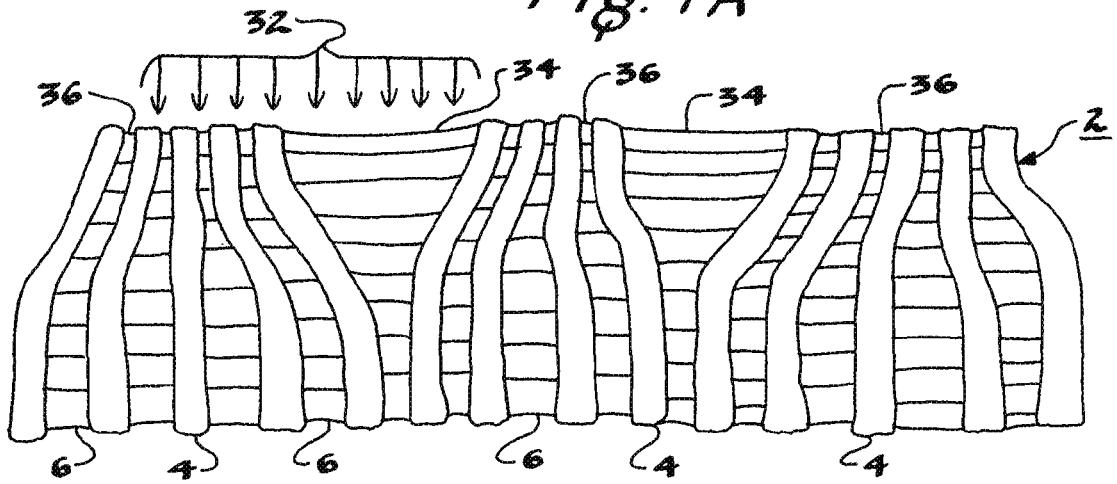
Figure 4C:
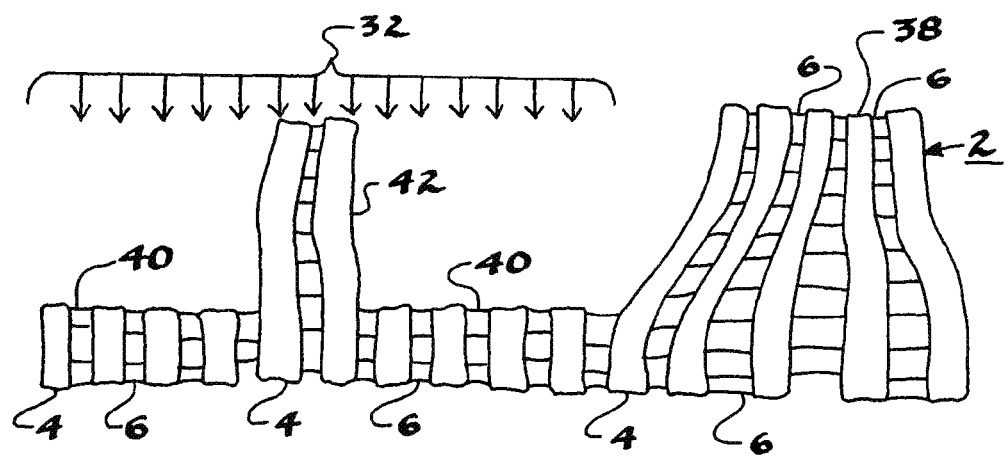

FIG. 4B is a partial cross-section view of the expanded PTFE material 2 during the initial exposure to laser energy 32. The initial exposure to the laser energy results in elongated fibrils 34 and shortened fibrils 36. As shown in FIG. 4C, continued exposure to the laser energy results in the removal of the surface portion of some nodes, along with the removal of the elongated fibrils. Thus a valley 40 is formed, along with a clustered, coalesced node structure 38, interconnected with fibrils 6. Disposed on the valley floor is the initial formation of a rough, gnarled node structure 42.

Figure 4D:
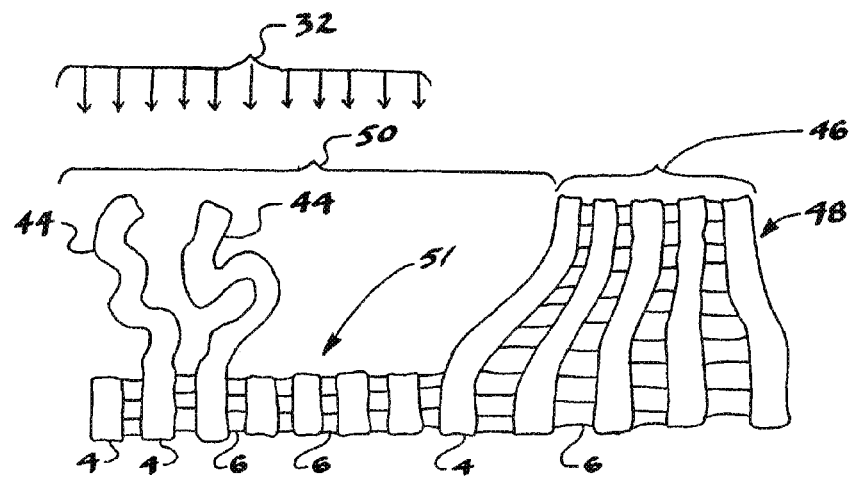

As shown in FIG. 4D, continued application of the laser energy 32 results in the formation of a ridge 48 comprising coalesced nodes 46 interconnected by fibrils 6. Valleys 50 are formed having a microstructure of nodes 4 interconnected by fibrils 6 on valley floor 51. Irregularly shaped gnarled node structures 44 remain in the valleys 50.

Figure 4E:
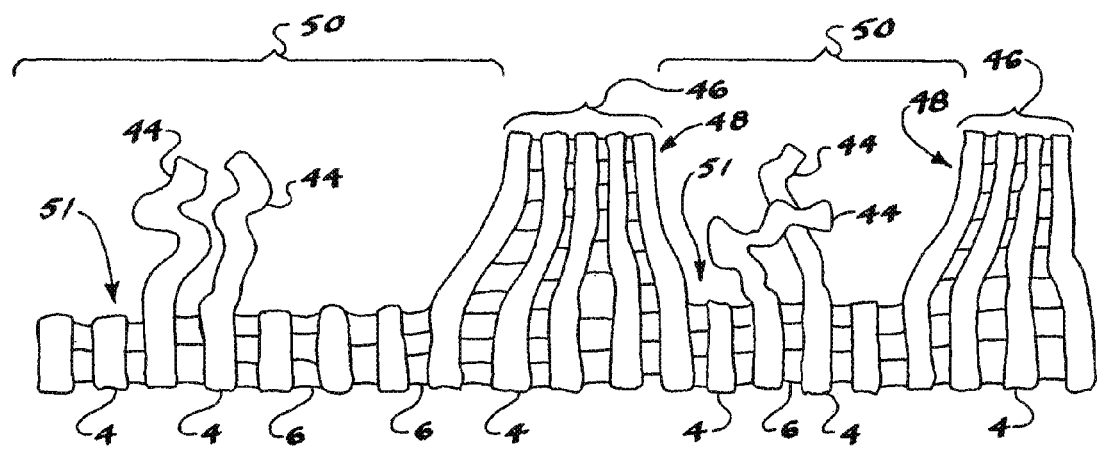

Shown in FIG. 4E is a partial cross-sectional view of an expanded PTFE surface after processing according to the present invention. Shown are ridges 48, valleys 50, coalesced node clusters 46, and the distorted, crooked, gnarled node structures 44.

Laser energy for the present invention should be generated by an unfocused laser beam delivering sufficient energy to the PTFE surface to cause PTFE surface alteration in the manner described. Specifically, it is preferred to use a $CO_2$ laser with a wavelength output of about 10.6 microns. Other lasers, such as Eximer, YAG, ruby, etc., may also be suitable for use with the present invention. It is preferred that the laser beam is "unfocused" so that energy is delivered over a wider path than a fully focused beam. The preferred beam width at contact with the surface is less than about 1 mm to 3 mm or more, with the most preferred width being between about 1.5 and 3 mm.

The amount of power delivered is a function of the speed of the laser beam's passage over the PTFE surface. For slow laser treatment, for instance at a movement of about 10 inches (25.4 cm) per minute, a low power laser down to about 20 Watts may be acceptable. For fast production applications, for instance at a movement of about 500 inches (1,270 cm) or more per second, a high powered laser up to about 1000 Watts or more may be required. As a balance between speed and power, laser wattage of about 350 Watts can treat at a rate of about 20 inches (50.8 cm) per second.

Similarly, the pulse duration and spacing of the laser beam delivery may also be adjusted. Laser settings may vary from a low of about 0.1 msec pulse duration at about 0.001 inch (0.254 mm) spacing, up to continuous delivery (for speeds above 200 inches (508 cm) per minute. Preferred delivery is about 1.5 msec pulse duration at about 0.005 inch (1.27 mm) spacing.

Figure 4F:
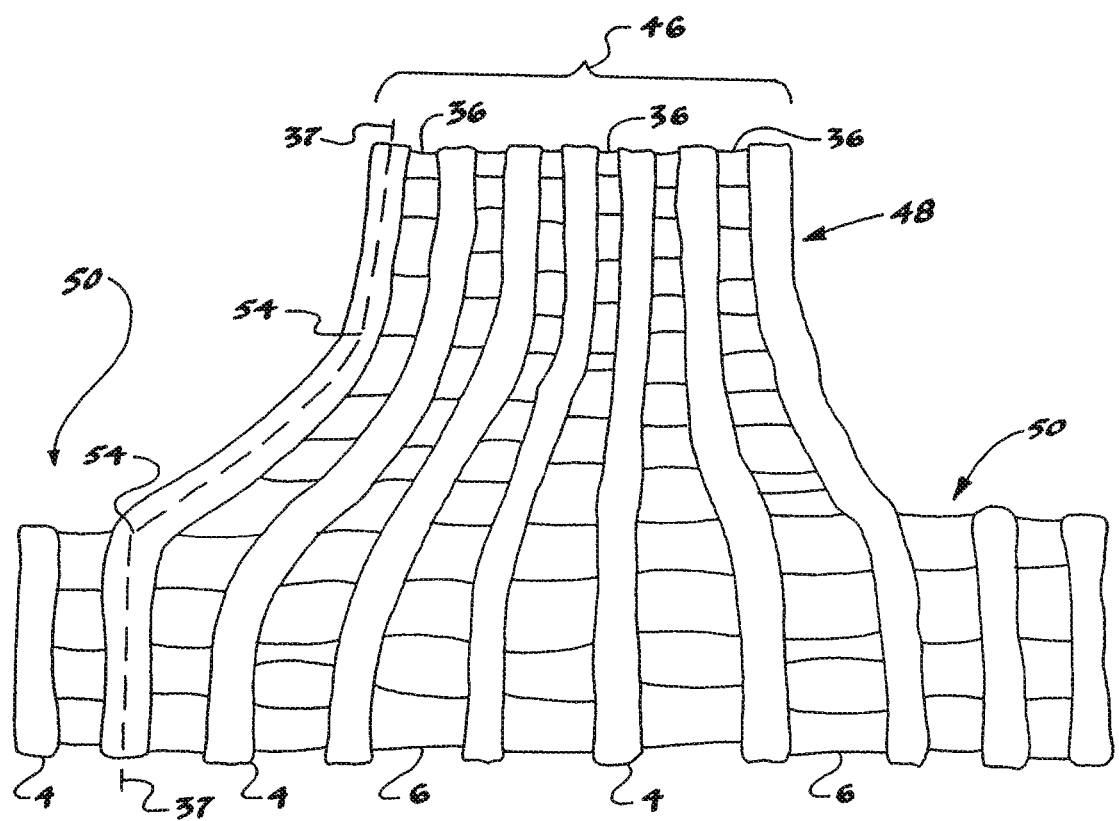

The characteristics and definition of a "node cluster" is further clarified by FIG. 4F. Illustrated are valleys 50 and a ridge 48 that is primarily formed by a node cluster 46. The node cluster 46 comprises nodes 4 interconnected by fibrils 6. The nodes 4 within the node cluster 46 are interconnected with shortened fibrils 36 on the outer, or treated, surface and interconnected with longer, untreated fibrils 6 in the lower portions of the material. The shortened fibril length causes the fibrils to bend, deflect together, and coalesce on the outer surface, as depicted in FIG. 4F. The shortened fibrils 36 are at least 25% shorter than the deeper untreated fibrils 6. As the term "node cluster" is used herein, it is a grouping of at least 5 nodes, the nodes being significantly interconnected on the outer surface, with fibrils that are at least 25% shorter (and more preferably at least 50% shorter) than the interconnecting fibrils of the untreated lower surface.

The exact form the "gnarled nodes" take may vary considerably from structure to structure due to differences in expanded PTFE precursor material and the exact processing parameters employed. As such, "gnarled nodes" may be identified as one or more of a number of similar structures that are defined below with reference to FIGS. 5 and 6A through 6D.

Figure 5:
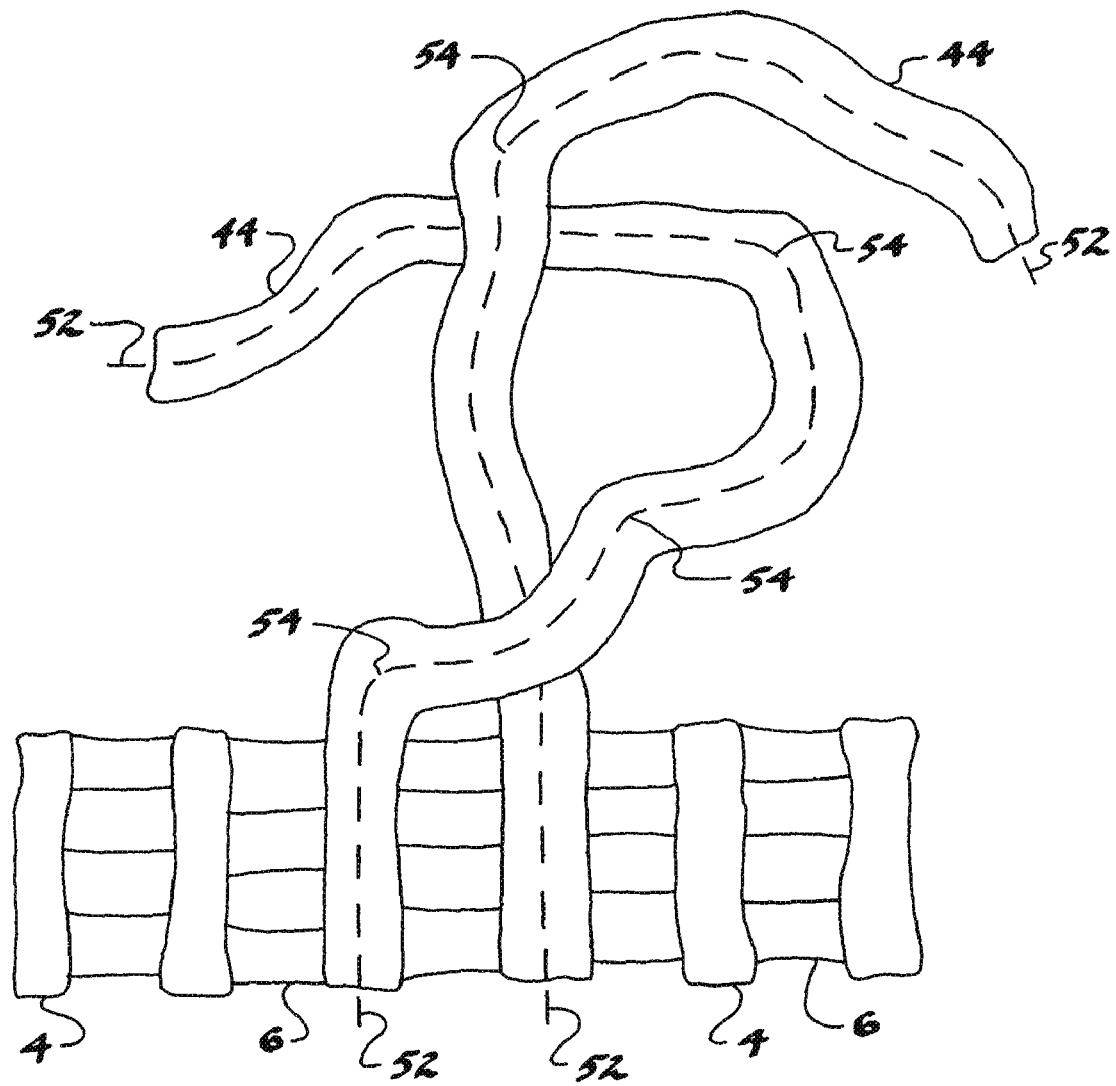
FIG. 5 is an enlarged partial side cross-section view detailing a gnarled node structure of the present invention.

The characteristics and definition of a "gnarled node structures" may first be clarified by reference to FIG. 5. Shown in FIG. 5 is a partial cross-section view of a gnarled node structure 44 having an angular or bent longitudinal axis 52. The angular or bent longitudinal axis 52 has a length that approximates the overall length of the gnarled node (that is, the entire length of the node extending into (and perhaps all the way through) the material (even beneath the floor of the valley)). The interconnecting fibrils 6 are absent along a substantial portion of the gnarled node length. A substantial portion of the gnarled node length is defined as more than 25% of the entire length of the gnarled node, and more preferably 50 to 75% or more of the entire length. The longitudinal axis 52 of the gnarled node also has at least two angular deflection points, or bends in the axis 54. An "angular deflection point" is defined as a bend or change of direction of at least 30 degrees of the node longitudinal axis. Thus a "gnarled node" can be identified as a node having at least two angular deflection points of at least 30 degrees along its longitudinal axis and being devoid of interconnecting fibrils along at least 25% of the entire node length.

Figure 6A:
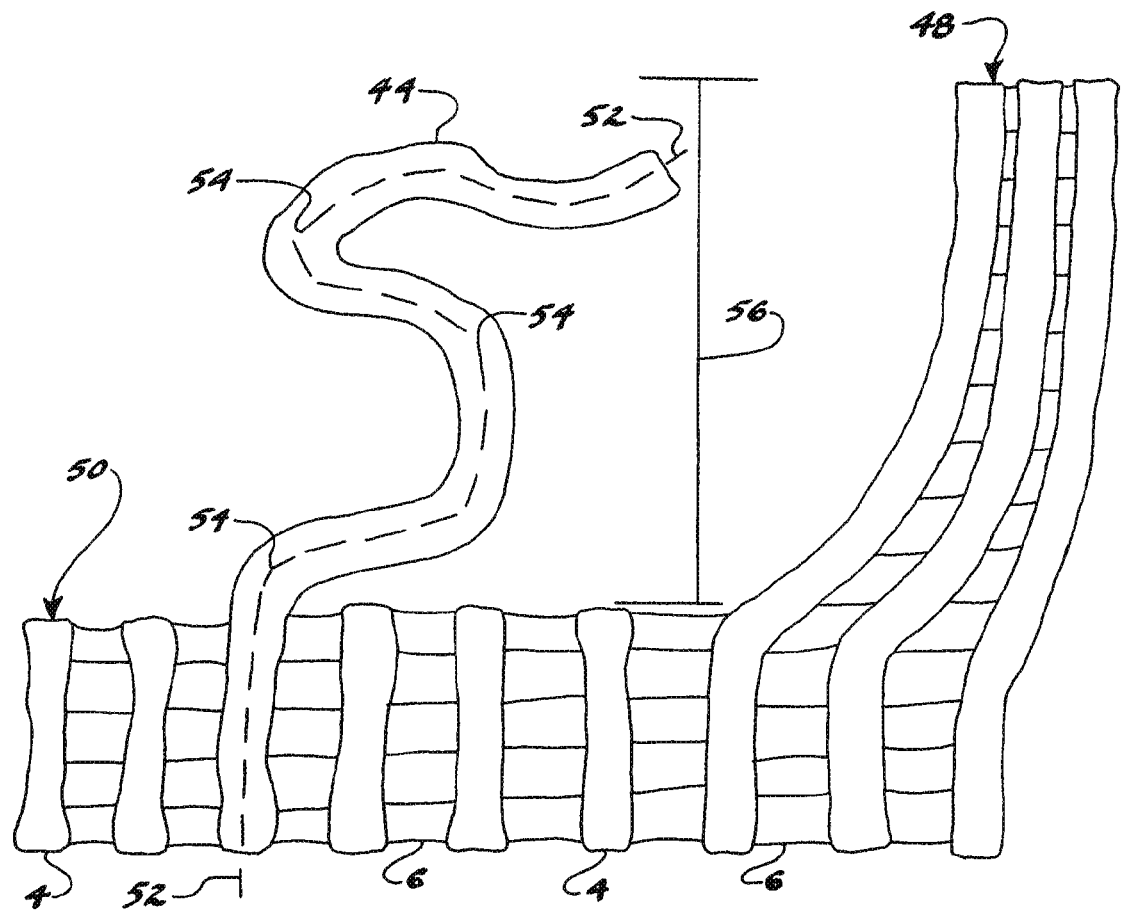
FIG. 6A is an enlarged partial side cross-section view further detailing a gnarled node structure of the present invention relative to one ridge.

FIG. 6A provides a further description of a "gnarled node." Shown in FIG. 6 A is a partial cross-sectional view of a gnarled node structure 44 having an angular or bent longitudinal axis 52. Again, the angular or bent longitudinal axis 52 has a length that approximates the overall length of the gnarled node. The interconnecting fibrils 6 are absent along a length of the gnarled node. The portion of the gnarled node length that is devoid of interconnecting fibrils is as least as long as (and, as is described below, can be even longer than) the approximate height 56 of an adjacent ridge. Again, the longitudinal axis 52 also has at least two angular deflection points or bends in the axis 54, of at least 30 degrees of the node longitudinal axis. Thus a gnarled node may also be identified as a node having at least two angular deflection points along its longitudinal axis, and the node being devoid of interconnecting fibrils along a length at least equal to the height of an adjacent ridge.

Surprisingly it has been determined that many gnarled nodes have a longitudinal axis length that is actually longer than the height of adjacent ridges. It is believed that this occurs as an artifact of the laser distortion process described in reference to FIGS. 4A through 4F, above, whereby the gnarled nodes are first stretched during laser treatment before breaking loose from the adjacent ridges to become freestanding. As a result, a gnarled node can be further identified as a node having a protruding (that is, exposed) length that is longer than the approximate height of an adjacent ridge 56 and the node being substantially devoid of fibrils along its protruding length.

Figure 6B:
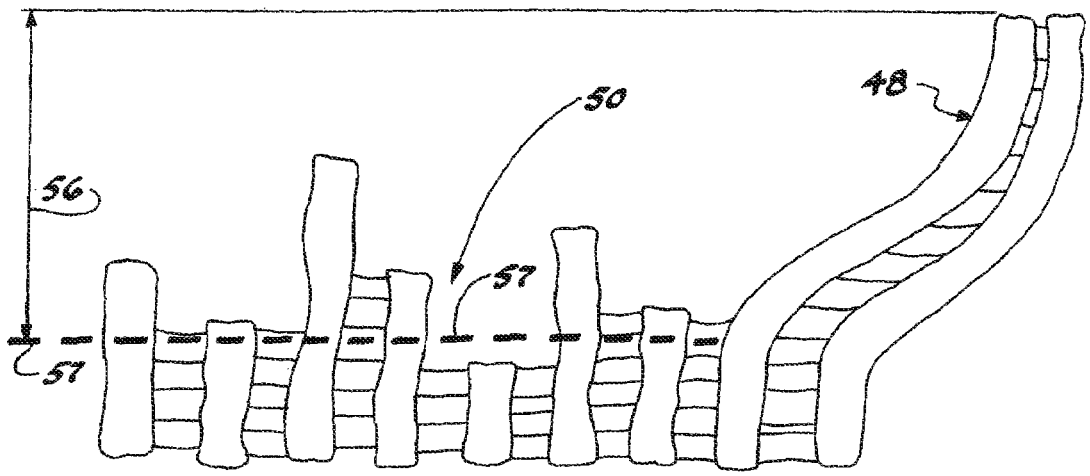
FIGS. 6B and 6C are enlarged partial side cross-section views of irregular or uneven valley floors and corresponding methods of determining the relative height of an adjacent ridge.
Figure 6C:
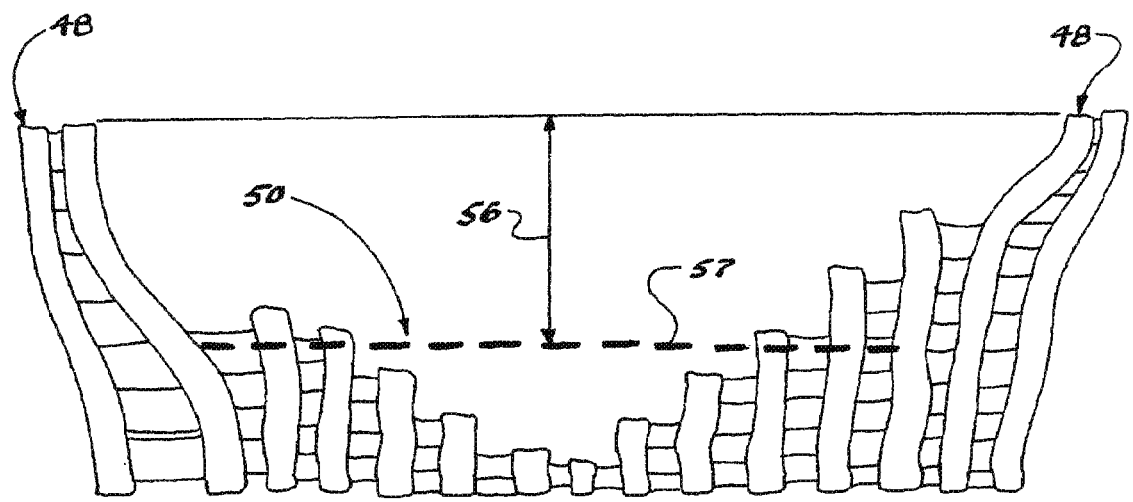

The "approximate height of an adjacent ridge" is further clarified and defined by FIGS. 6B and 6C, which show valleys 50 having an irregular or uneven valley surface or floor. In these or similar configurations having uneven valley floors, the height of an adjacent ridge 56 may be approximated by establishing an average valley floor plane 57. The average valley floor plane 57 can be visually determined by enlarged visual inspection approximating a plane at a depth equal to the average height of the valley floor nodes, which do not include gnarled nodes, as illustrated in FIGS. 6B and 6C.

Figure 6D:
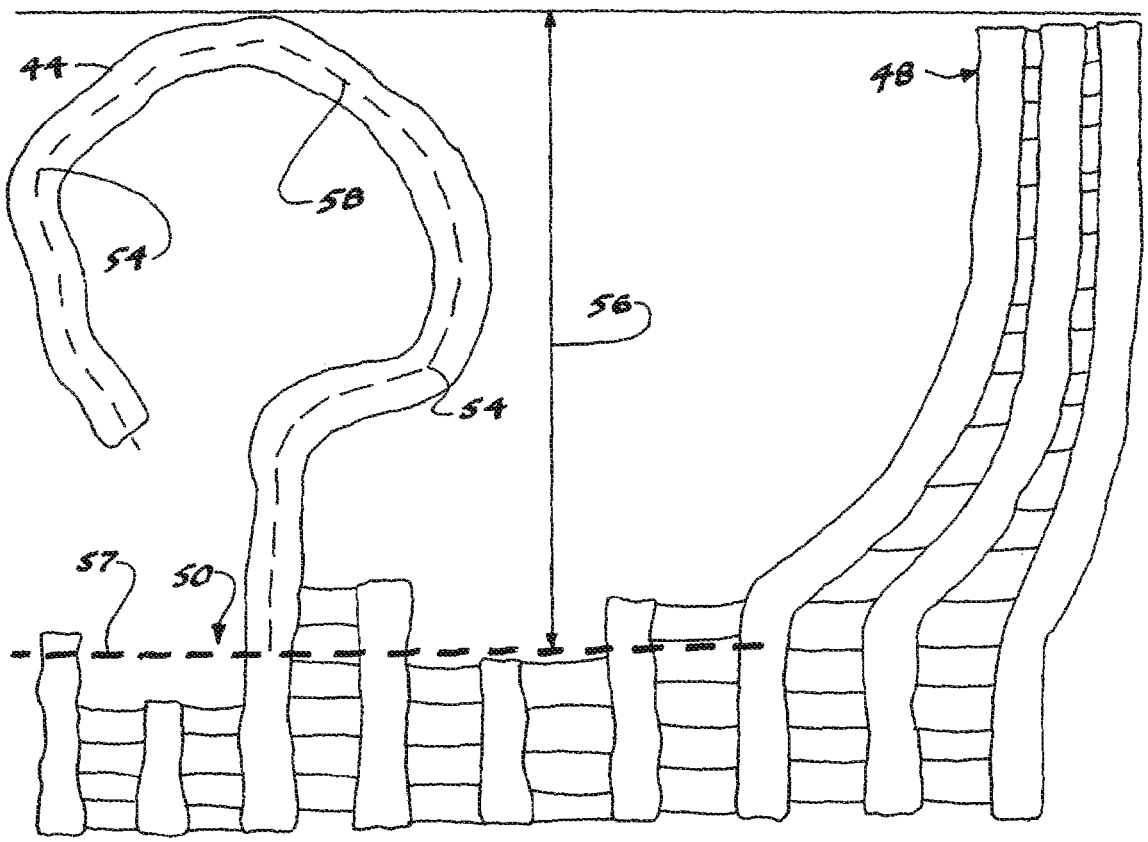
FIG. 6D is an enlarged partial cross-section side view of a gnarled node of the present invention illustrating its longitudinal axis, which defines the length of the node projecting from the valley floor.

Shown in FIG. 6D are a ridge 48, a valley 50, an average valley floor plane 57, and a gnarled node 44. The gnarled node 44 has a partial longitudinal axis 58 that transverses the portion of the gnarled node protruding from the average valley floor plane 57. Thus, the length of the axis 58 defines the protruding length of the gnarled node measured from the average valley floor plane 57. Again, the axis 58 has angular deflection points 54, as previously defined. Accordingly, a gnarled node may also be determined as a node having at least two angular deflection points along its longitudinal axis, and the node being substantially devoid of interconnecting fibrils along its protruding length.

Groupings of adjacent gnarled nodes may have the additional attribute of being twisted, entwined, and/or interlocked together. This interaction of adjacent gnarled nodes can add additional degrees of stiffness, macro-roughness, and texturing to a small cluster or grouping of gnarled nodes.

By way of example, in a preferred embodiment of the present invention, GORE-TEX® Soft Tissue Patch, available from W. L. Gore and Associates, Inc., Flagstaff, Ariz., is used as an expanded PTFE precursor material for the process of the present invention. The expanded PTFE patch material is initially placed onto a fixture having vertical pins located along the periphery of the patch material to be treated. The patch material is forced over and punctured by the periphery pins on the holding fixture. The patch material is thus constrained from significant contraction and is maintained in an essentially planer state. The fixture and patch are then located onto a laser.

A preferred laser is an 80 watt CO2 laser, procured from Laser Machining, Inc., 500 Laser Drive, Somerset, Wis., 54025, Model number C-42. Such a laser has a directed energy, or laser beam output. The approximate, preferred process parameters are set as follows: output power of 70 watts, cutting head vacuum of 30 mbar, pulse spacing of 0.13 mm (0.005") and pulse duration of 1.5 milliseconds. The focusing, or final lens set, is removed, resulting in an "unfocused" laser beam having an approximate diameter of about 2.5 mm (0.1"). The laser beam is still highly collimated and the removal of the focusing lenses eliminates the highly focused, convergence of the beam, which is normally used in cutting or welding applications.

The approximate distance between the laser beam turn-down mirror and the sheet being treated is determined by the specific laser used and in a preferred case is about 40 cm. A specific pattern is then used to expose the constrained patch material to the laser beam. As is explained in greater detail below, the exact pattern to be applied may be take a variety of forms. One possible exposure pattern is a serpentine path having a pattern center to center spacing of approximately 3.8 mm (0.15") and table motion speed of approximately 2.5 m/min (100"/min.). One serpentine path comprises essentially parallel, straight-line segments, over the patch area to be treated and 180°turns, of approximate 3.8 mm (0.15") diameter, occurring outside of the patch area to be treated. The laser is cycled off during the 180° turns. Thus the patch material is exposed to a laser energy pattern of essentially straight, parallel repeating lines. The resulting expanded PTFE treated surface has a linear striping ("ribbed") appearance.

The process of the present invention can be employed to establish ridge and valley structures of a wide variety of shapes and dimensions. In the example above, the final ribbed structure has a ridge height (or valley depth) of about 0.3 mm (0.01 inch) and a centerline to centerline distance between ridges of about 3.8 mm (0.15 inch). For implantable patch material in most cases, it is believed to be generally preferred to have ribbed material dimensions with a ridge height of about 0.1 to 1 mm (0.004 to 0.04 inch) and a centerline to centerline distance between ridges of about 0.2 to 13 mm (0.01 to 0.5 inch).

Figure 7:
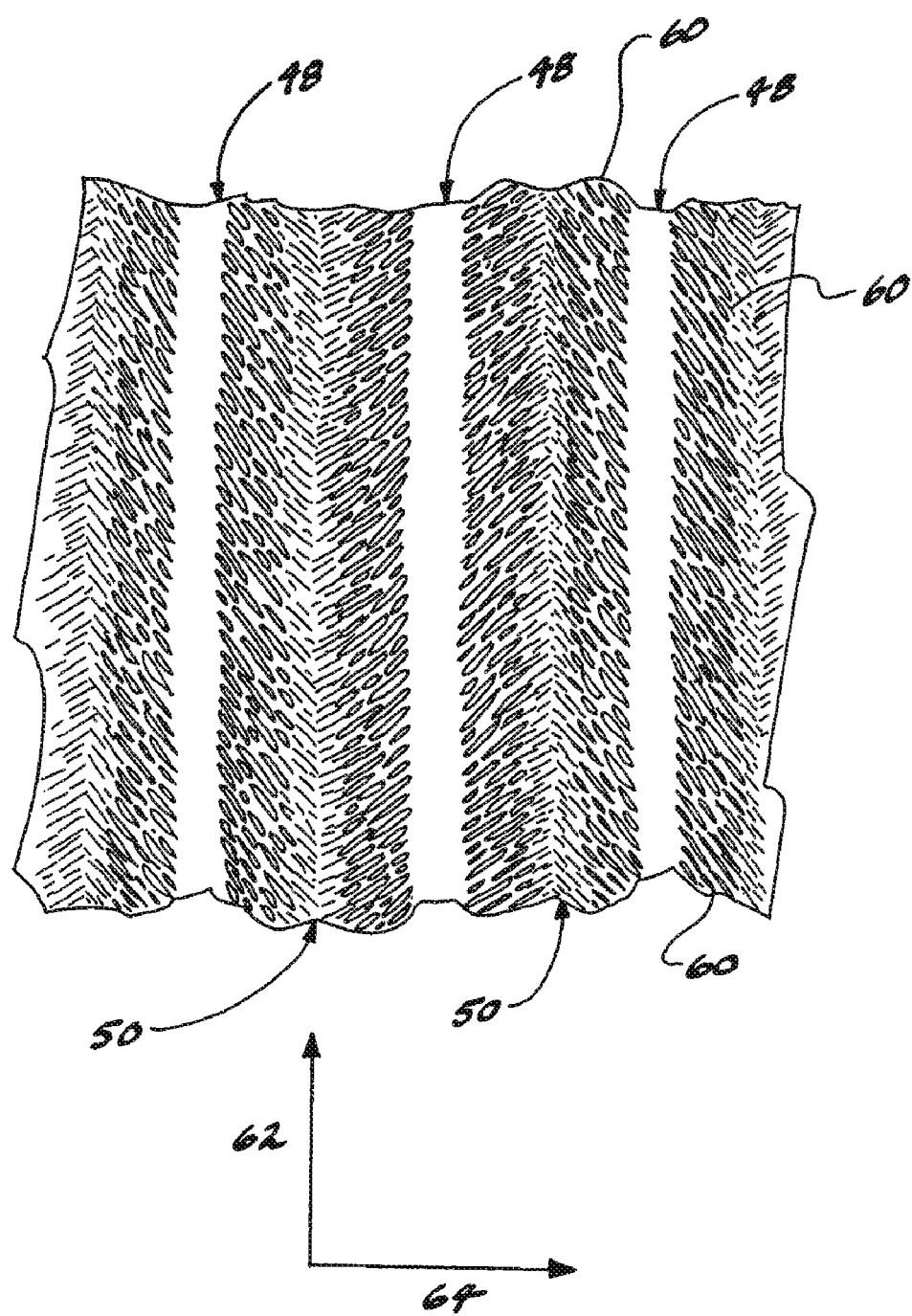
FIG. 7 is a top plan view of an expanded PTFE sheet of the present invention after being exposed to alternating rows of laser treatment of the present invention.
Figure 9A:
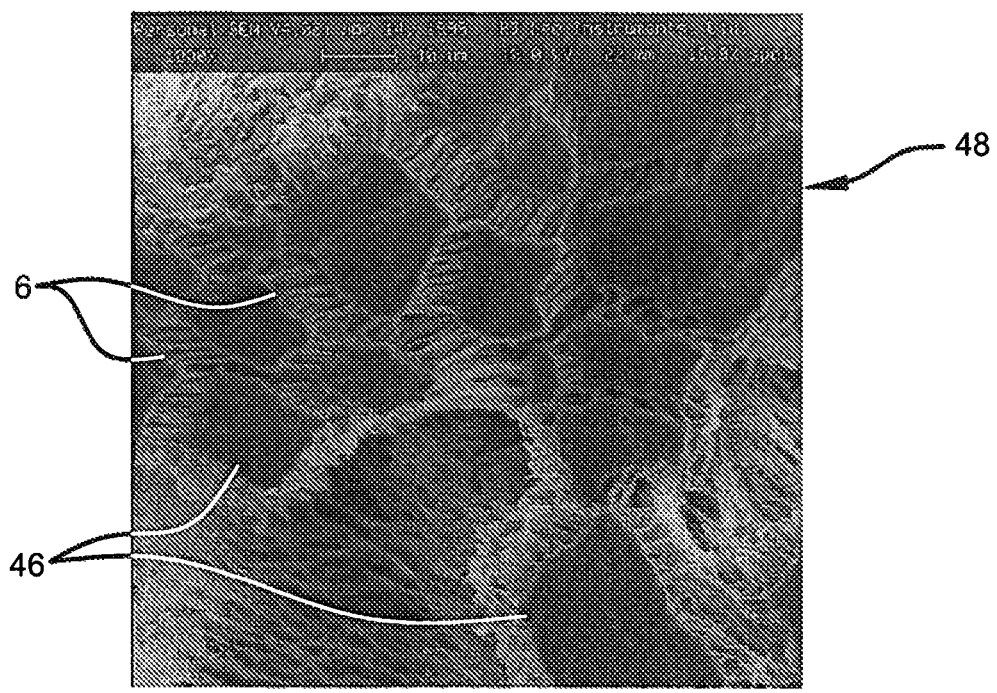
FIG. 9A is a scanning electron micrographs (S.E.M.s), enlarged 1000×, top view of coalesced nodes along a ridge of the present invention.
Figure 9B:
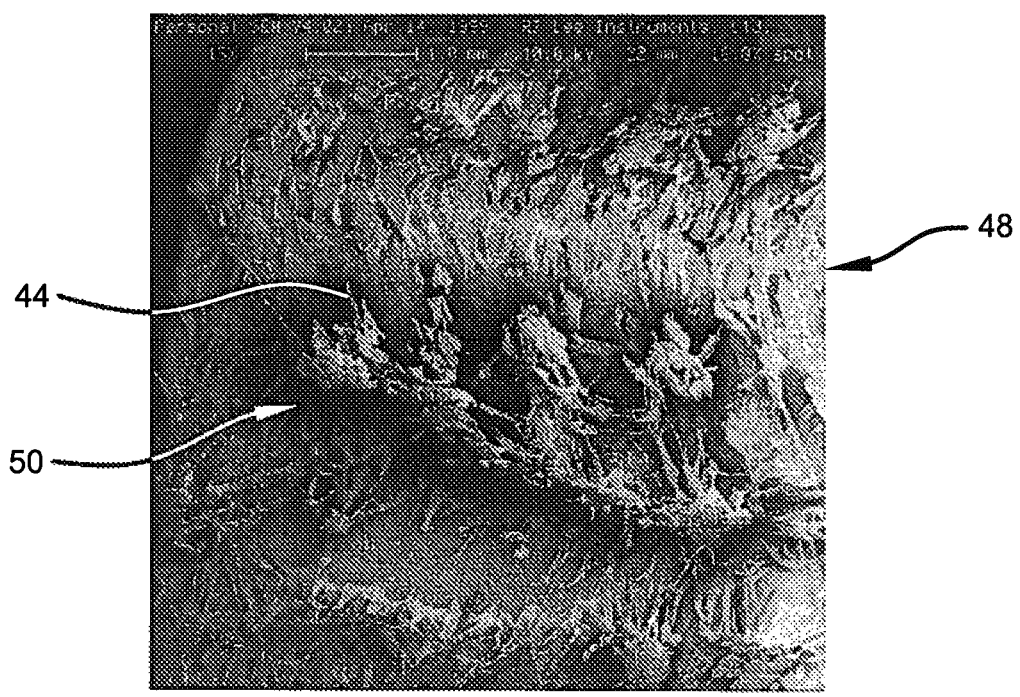
FIG. 9B is an S.E.M., enlarged 15×, top view of ridge, valley, and gnarled nodes of the present invention.
Figure 9C:
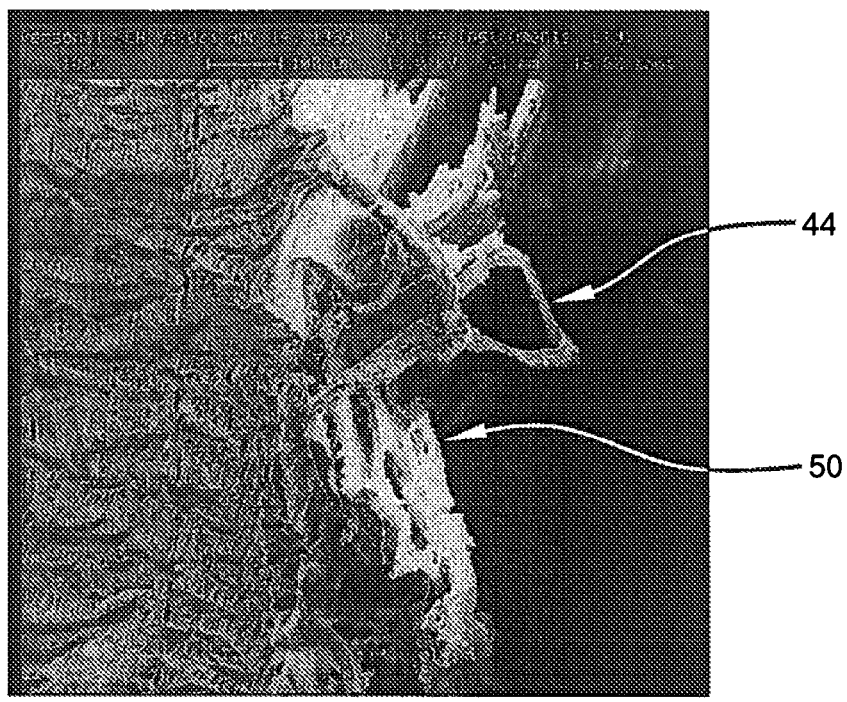
FIG. 9C is an S.E.M., enlarged 100×, cross-section side view of a valley and gnarled nodes of the present invention.
Figure 9D:
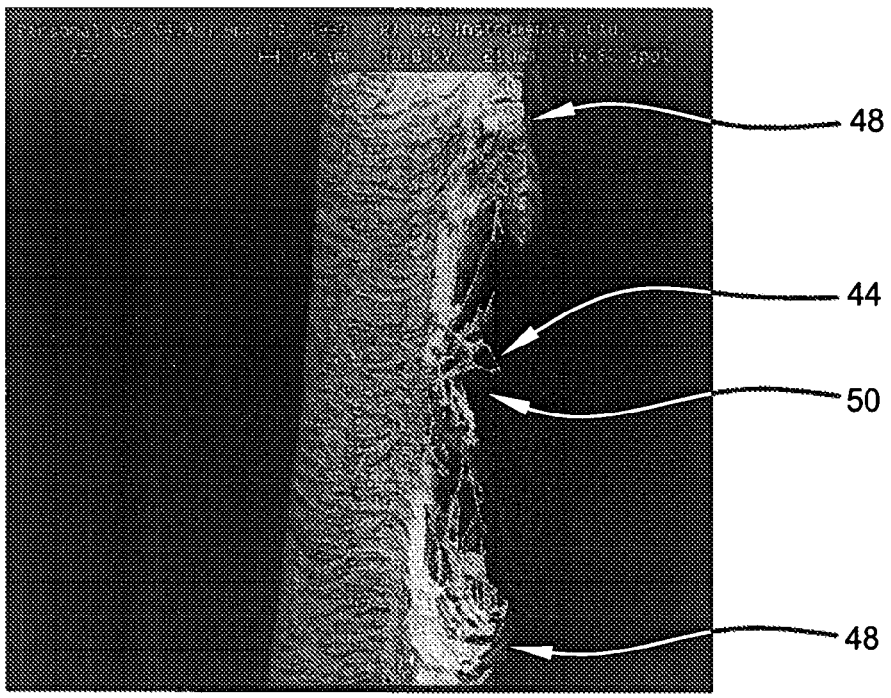
FIG. 9D is an S.E.M., enlarged 25×, cross-section side view of ridges, a valley, and gnarled nodes of the present invention.

Shown in FIG. 7 is a typical top surface view of an expanded PTFE sheet after being exposed to a treatment of the present invention. Shown are ridges 48, valleys 50, and angular clusters of gnarled nodes 60. The laser exposure essentially occurred over the valleys, parallel to the vertical axis 62. Present on, and projecting from, the valley floors are clusters of gnarled nodes 60, oriented approximately 45 degrees to the vertical axis 62. The 45° orientation of the valley node clusters renders a "herringbone" appearance to the treated surface. This angular orientation of the gnarled node clusters also imparts a "directionality" to specific physical properties of the treated surface. For example, the static and sliding friction can vary depending upon the direction of relative motion between the treated sheet and another material. For example, coefficients of friction will vary if a material is moved "along with" or "against" the direction of the herringbone pattern, as depicted by axis 62. The coefficients of friction will also be affected if the relative motion is along axis 64 compared to axis 62. Thus different coefficients of friction can be derived depending upon the directions of relative motion.

Other physical properties having a "directionality" relative to the treated surface, or being affected by the treated surface, may include, but are not limited to, liquid roll-off angle, flow turbulence or resistance, sound reflection or abatement, abrasion, ablation, bond peel strength, mass transfer and heat transfer. In addition the absorption, reflectance or transmission of electromagnetic energy, including the visible spectrum, can be altered or have "directionality" imparted to, by the surface treatment of the present invention. The laser treatment process parameters can be manipulated to produce other patterns and textures. The focusing lenses may be replaced and the process of the present invention can be used to generate finely detailed, small geometry patterns.

Shown in FIGS. 8A through 8I, are various patterns that may be used to treat surfaces according to the present invention. Shown in FIG. 8A is a serpentine laser pattern 70 and a typical surface outline 72. Shown in FIGS. 8B through 8I are alternate examples of possible patterns. Shown in FIGS. 8B through 8E are serpentine, wave-like and two axes crossing patterns 70 used to generate specific textures or patterns. A mask can be used to expose and generate a wide variety of patterns. For example, a stainless steel mask, having an array of circular holes, can be placed over the sheet material prior to laser exposure, generating a pattern as shown in FIG. 8F. Alternately, shaped masking holes can generate patterns such as depicted in FIG. 8G. Exposure patterns can also include alpha and numeric symbols for lot numbers, part numbers, dates, etc., such as depicted in FIG. 8H. In addition, symbols, such as trademarks, logos, etc., can be generated and textured onto a surface, as shown in FIG. 8I. Multiple patterns of exposure can be utilized, for example the pattern of FIG. 8B can be superimposed onto the pattern of FIG. 8F.

The process of the present invention is not limited to planer surfaces. The unfocused laser beam is relatively insensitive to the distance between the laser turn-down mirror and the surface being treated, therefore the laser has a long "depth of field" along the vertical axis. The process of the present invention is therefore well suited for the treatment of highly irregular, three-dimensional surfaces. By the incorporation of additional controlled motion axes, forms such as tubes, rods or items with polygon shaped cross-sections can be treated using the process of the present invention.

FIGS. 9 A through D are scanning electron microscope (S.E.M.) photographs, showing various expanded PTFE surfaces treated by the process of the present invention. These S.E.M.s illustrate the ridges 48, valleys 50, coalesced nodes 46, fibrils 6, and gnarled nodes 44 of the present invention.

Figure 10:
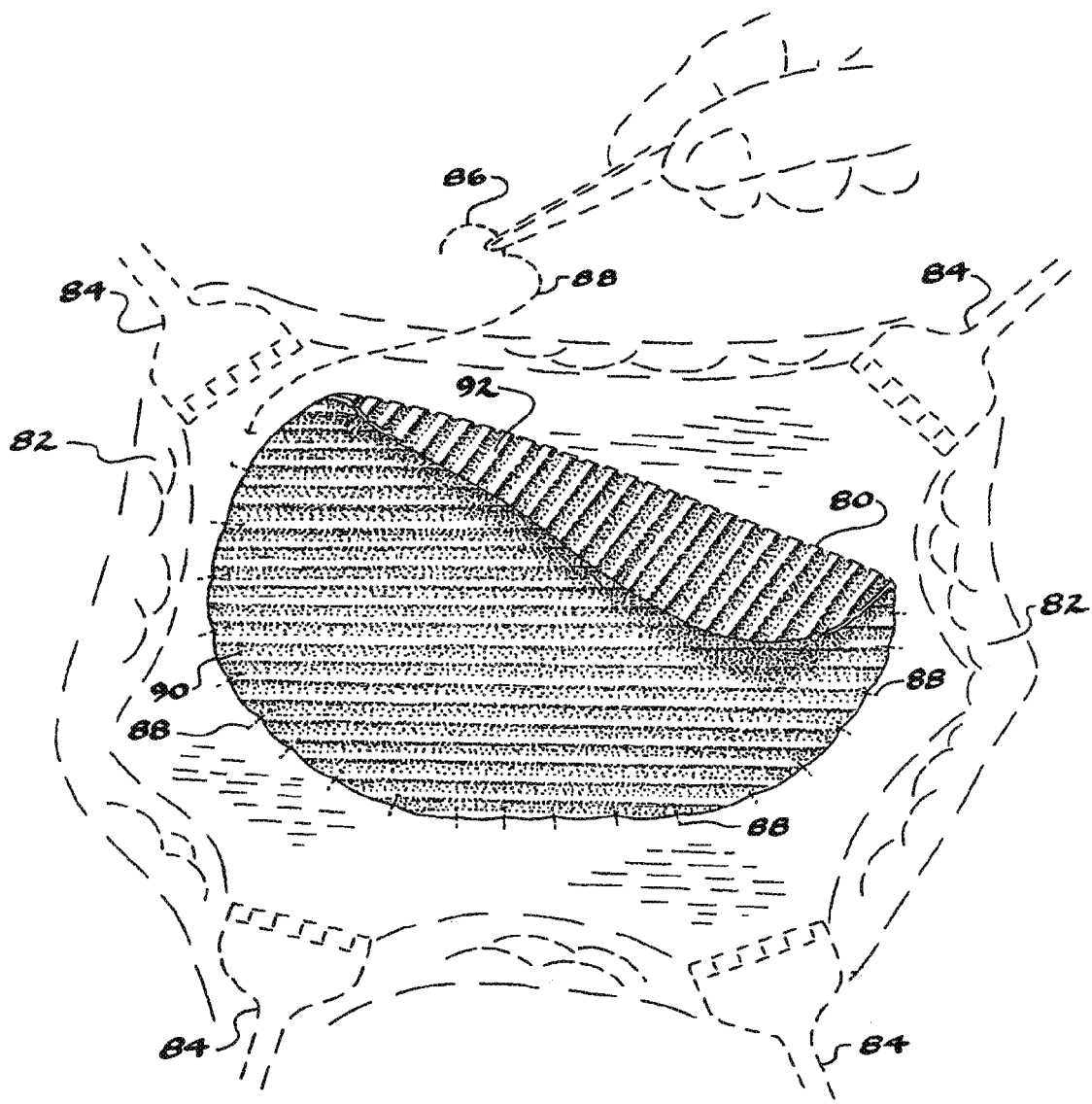
FIG. 10 is a three-quarter isometric view of a surgical sheet modified in accordance with the present invention being implanted, the sheet having two surfaces treated by the process of the present invention.

Shown in FIG. 10, is an implantable patch or sheet 80 being placed in a sub-dermal location in a patient during a tissue repair procedure. Shown is tissue 82, tissue retractors 84, suture needle 86, and suture 88. The outside (or dermal) surface 90 of the repair patch 80 has been treated by the process of the present invention. The opposing surface 92 has also been treated by the process of the present invention. The treated surfaces 90, 92 have both a highly porous node and fibril microstructure along with a high degree of texturing or roughness. The treated surfaces thus encourage and promote rapid tissue ingrowth and attachment, which anchors and secures the repair sheet 80 to the tissue 82. The ingrowth therefore enhances the attachment strength of the repair sheet to the tissue, beyond that of the sutures alone.

It should be evident from the above description that the present invention has a wide variety of possible uses in numerous applications, including in medical, industrial, electronic, and consumer products. Other changes and modifications of the present invention may be incorporated without departing from its intent. For instance, although microporosity can be maintained in the process of the present invention, it may be desirable in certain applications to partially or completely fill the microporous structure to provide other desirable features (such as liquid impermeability).

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. A continuous process for modifying a material surface, comprising the steps of:
   a) providing an expanded polytetrafluoroethylene material having a surface comprised of nodes interconnected by fibrils, the fibrils having lengths;
   b) exposing the expanded polytetrafluoroethylene surface to an unfocused laser beam to elongate fibrils and shorten fibrils to form node clusters;
   c) exposing the polytetrafluoroethylene surface having said node clusters to an unfocused laser beam to remove the surface portion of some nodes and some elongated fibrils, thereby producing a material having said node clusters, valleys, and rough gnarled nodes connected by fibrils disposed on the valley floor; and, next
   d) exposing the material having said node clusters, valleys, and said rough gnarled nodes connected by fibrils, to an unfocused laser beam to remove the fibrils connecting said rough gnarled nodes to form gnarled nodes, said gnarled nodes having a protruding length and being substantially devoid of fibrils along the protruding length.

2. The process of claim 1 wherein the node clusters have a height and further comprises forming the gnarled nodes so that the protruding length of the gnarled node is greater than the height of the node clusters.

3. The process of claim 1 that further comprises forming a pattern of parallel groves in the surface.

4. The process of claim 1 that further comprises the unfocused laser beam having a width applied to the surface of between about 1.5 and 3 mm.

5. The process of claim 1 that further comprises providing a surface of expanded polytetrafluoroethylene comprising an implantable medical device.

* * * * *